(12) United States Patent
Oxley

(10) Patent No.: US 12,357,814 B2
(45) Date of Patent: Jul. 15, 2025

(54) SYSTEMS AND METHODS FOR DEEP BRAIN STIMULATION

(71) Applicant: The University of Melbourne, The University of Melbourne (AU)

(72) Inventor: Thomas James Oxley, New York, NY (US)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 16/405,798

(22) Filed: May 7, 2019

(65) Prior Publication Data
US 2019/0336748 A1 Nov. 7, 2019

Related U.S. Application Data

(60) Provisional application No. 62/667,987, filed on May 7, 2018.

(51) Int. Cl.
*A61N 1/05* (2006.01)
*A61N 1/36* (2006.01)

(52) U.S. Cl.
CPC ......... *A61N 1/0534* (2013.01); *A61N 1/0539* (2013.01); *A61N 1/36067* (2013.01); *A61N 1/36075* (2013.01); *A61N 1/36096* (2013.01); *A61N 1/36139* (2013.01)

(58) Field of Classification Search
CPC ............... A61N 1/0534; A61N 1/0539; A61N 1/36067; A61N 1/36075; A61N 1/36096; A61N 1/36139; A61N 1/36185; A61N 1/0529; A61N 1/05; A61N 1/0536; A61N 1/36082; A61N 1/36071; A61N 1/36132; A61N 1/36135

USPC .................................................. 607/1, 2, 45
See application file for complete search history.

(56) References Cited

U.S. PATENT DOCUMENTS

| | | | | |
|---|---|---|---|---|
| 2007/0255379 | A1* | 11/2007 | Williams | A61N 1/05 607/120 |
| 2008/0312715 | A1* | 12/2008 | Asirvatham | A61B 5/6851 607/45 |
| 2011/0040546 | A1* | 2/2011 | Gerber | A61N 1/37 703/11 |
| 2014/0066949 | A1* | 3/2014 | Eskuri | A61N 1/36082 607/45 |

(Continued)

OTHER PUBLICATIONS

Che-Chang Yang, A Review of Accelerometry-Based Wearable Motion Detectors for Physical Activity Monitoring, 2010, NCBI, vol. 10 (Year: 2010).*

*Primary Examiner* — Jennifer Pitrak McDonald
*Assistant Examiner* — Michael T. Holtzclaw
(74) *Attorney, Agent, or Firm* — Levine Bagade Han LLP

(57) ABSTRACT

The present invention involves methods of stimulating tissue using one or more series of electrodes to apply energy through a combination of electrodes to stimulate various regions within an area of interest. Such an approach can triangulate areas where stimulation and/or treatment is needed for deep brain stimulation (DBS). In addition, the triangulation system and methods described herein can be applied to any portion of a body where stimulation of a particular area is required while using the vascular network to access tissue surrounding that particular area so that a combination of electrodes can be used to identify the region of interest that requires stimulation.

13 Claims, 7 Drawing Sheets

(56) References Cited

U.S. PATENT DOCUMENTS

| | | | |
|---|---|---|---|
| 2016/0136427 A1* | 5/2016 | De Ridder | A61N 1/36082 |
| | | | 607/45 |
| 2018/0236221 A1* | 8/2018 | Opie | A61N 1/0531 |
| 2018/0318575 A1* | 11/2018 | Gross | A61N 1/0536 |
| 2019/0134401 A1* | 5/2019 | Schouenborg | A61N 1/378 |

* cited by examiner

SYSTEMS AND METHODS FOR DEEP BRAIN STIMULATION

CROSS-REFERENCE TO RELATED APPLICATIONS

This application claims benefit of priority to U.S. Provisional Patent Application No. 62/667,987 filed May 7, 2018, the content of which is incorporated herein by reference in its entirety.

BACKGROUND OF THE INVENTION

Deep brain stimulation ("DBS") involves implanting electrodes within certain areas of a brain where the electrodes produce electrical impulses in an attempt to stimulate or regulate brain activity for a therapeutic purpose. The simulation of the brain can regulate abnormal impulses and/or can affect certain cells and chemicals within the brain.

DBS involves creating small holes in the skull to implant the electrodes, and surgery to implant a controller or pacemaker-like device that is electrically coupled to the electrodes to control the stimulation. Typically, this device is positioned under the skin in the chest. The amount of stimulation in deep brain stimulation can be controlled by the controller or pacemaker-like device where a wire/lead connects the controller device to electrodes positioned in the brain.

DBS can be used to treat a number of neurological conditions, such as tremors, Parkinson's disease, dystonia, epilepsy, Tourette syndrome, chronic pain, and obsessive compulsive disorder. In addition, Deep brain stimulation has the potential for treatment of major depression, stroke recovery, addiction and dementia.

Deep brain stimulation also requires creating one or more small holes in the skull/cranium to implant electrodes, and surgery to implant a lead connecting the electrodes to the controller device.

FIG. 1 illustrates a conventional deep brain stimulation device 20 containing electrodes 22 that are implanted within a brain 12 of an individual 10. As shown, the implantation requires surgical penetration of the cranium 14 by the device 20 such that the device 20 is directed towards an area of interest 30. In addition, a lead 16 couples the device 20 to a controller/pacemaker 18. There are a number of risks associated with the general surgery required to surgically implant the device 20 in conventional DBS procedures. Furthermore, there are risks in the process of the DBS procedure itself given that conventional procedures require an approximation or non-invasive attempt to locate the region of interest 30. Then, the physician must attempt to physically position the electrodes 22 of the device 20 in or near the area of interest 30 such that the desired effect can be achieved. In certain cases, the positioning of the electrodes 20 can be a trial-and-error approach requiring multiple surgical attempts and multiple surgical insertion sites. Regardless of the number of attempts, the act of inserting the device 20 to position the electrodes 22 in the area of interest 30 creates collateral damage to brain tissue located in the path between the area of interest and the insertion point in the cranium.

Currently, the surgical risks involved in the DBS procedure can include bleeding in the brain, stroke, infection, collateral damage to brain tissue, collateral damage to vascular structures in the brain, temporary pain and inflammation at the surgical site. Apart from the surgical risks in conventional DBS involves risks in side effects of DBS if the electrodes stimulate or affect areas outside of the area of interest 30. Such risks can include breathing problems, nausea, heart problems, seizures, headache, confusion, etc. Yet an additional risk can be introduced upon attempting to remove a DBS device after a period of time given that tissue can heal around the device and implantation site.

There are also mild side effects associated with DBS including numbness or tingling sensations; muscle tightness of the face or arm; speech problems; balance problems; lightheadedness; undesired mood changes, which in extreme cases can produce mania and depression. Typically, the patient and/or physician attempts to mediate the side effects by adjusting the stimulation parameters, but doing so might cause a tradeoff in the effectiveness of the DBS to treat the original condition for which the DBS attempted to remedy.

There remains a need to address the problems with DBS and/or to improve current DBS effectiveness. The above is a brief description of some deficiencies in the conventional approach to DBS. The following disclosure describes some advantages and improvements to DBS. However, the following disclosure is meant as an example and variations are within the scope of the disclosure. Such variation can include a combination of embodiments or combinations of aspects of embodiments wherever possible. Furthermore, the following description of improved DBS can be combined with conventional DBS. Other features, advantages, and embodiments of the invention will be apparent to those skilled in the art from the following description and accompanying drawings, wherein, for purposes of illustration only, specific forms of the invention are set forth in detail.

SUMMARY OF THE INVENTION

The present invention involves methods of stimulating tissue using one or more series of electrodes to apply energy through a combination of electrodes to stimulate various regions within an area of interest. Such an approach can triangulate areas where stimulation and/or treatment is needed for deep brain stimulation (DBS). In addition, the triangulation system and methods described herein can be applied to any portion of a body where stimulation of a particular area is required while using the vascular network to access tissue surrounding that particular area so that a combination of electrodes can be used to identify the region of interest that requires stimulation.

In one example, the present disclosure includes a method of stimulating a cerebral tissue of a brain, where the cerebral tissue is associated with a brain activity of an individual. For example, such a method can include positioning a first series of electrodes in a first vascular location in a first region of the brain; positioning a second series of electrodes along a second vascular location in a second region of the brain; where the first region of the brain and the second region of the brain are adjacent to and spaced from the region in the cerebral tissue of the brain that is associated with the brain activity, and where the first region of the brain is spaced from the second region of the brain; repeatedly applying stimulation energy to a plurality of combination of electrodes selected from the first series of electrodes and/or the second series of electrodes, where application of energy to each of combination of electrodes produces an associated stimulated area of cerebral tissue respectively associated with that combination of electrodes; and identifying a target combination of electrodes where the associated stimulated area of cerebral tissue affects the brain activity.

In another variation, the methods described herein can include a variation where the plurality of combination of electrodes comprises at least three electrodes selected from the first series of electrodes and/or the second series of electrodes.

The described herein can affect brain activity that relates to a muscle or motor movement of the patient.

Variations of the method can include further comprising monitoring a portion of the individual for movement and associating increased or decreased movement of the portion of the individual when applying stimulation to the target region using the target combination of electrodes.

The methods described herein can include monitoring the portion of the individual for movement comprises using an accelerometer device on a hand or leg of the individual.

Another variation includes repeatedly applying stimulation energy to the plurality of combination of electrodes selected from the first series of electrodes and/or the second series of electrodes comprises determining every permutation of at least three electrodes and applying stimulation energy to every permutation until identifying the target combination of electrodes and the target region.

The method can further include applying a therapeutic energy to the target combination of electrodes to treat the target region. The therapeutic energy can be applied to the region using at least one second therapy electrode device.

In some variations, it might be necessary to pause between applying stimulation energy to each combination of electrodes.

The methods described herein can position the electrodes in a vessel of the brain, a vessel of the body, or in an area of tissue outside of a vessel but accessed through a vascular approach.

The methods described herein can further include obtaining a non-invasive image of the brain to correlate the target region with at least one anatomical feature.

In certain variations, the methods described herein can further comprise a first elongate structure carrying the first series of electrodes, the method further comprising anchoring the first elongate structure in the first region of the brain.

In certain variations, the methods described herein can further comprise anchoring the second elongate structure in the second region of the brain.

In another variation, the method can include a method of applying stimulation to tissue in a body of an individual. For example, such a method can comprise positioning a first series of electrodes in a first vascular location in a first region of the body; positioning a second series of electrodes along a second vascular location in a second region of the body; where the first region of the tissue and the second region of the body are adjacent to and spaced from the target region, where the target region is associated with a bodily function, and where the first region of the body is spaced from the second region of the body; repeatedly applying stimulation energy to a plurality of combination of electrodes selected from the first series of electrodes and/or the second series of electrodes, where application of energy to each of combination of electrodes produces an associated stimulated area of a tissue region in the body that is associated with that combination of electrodes; and identifying a target combination of electrodes where the associated stimulated area of a tissue affects the bodily function.

In a variation of the method above the first region of the body or the second region of the body comprises a vascular body.

DETAILED DESCRIPTION

Figure 1:
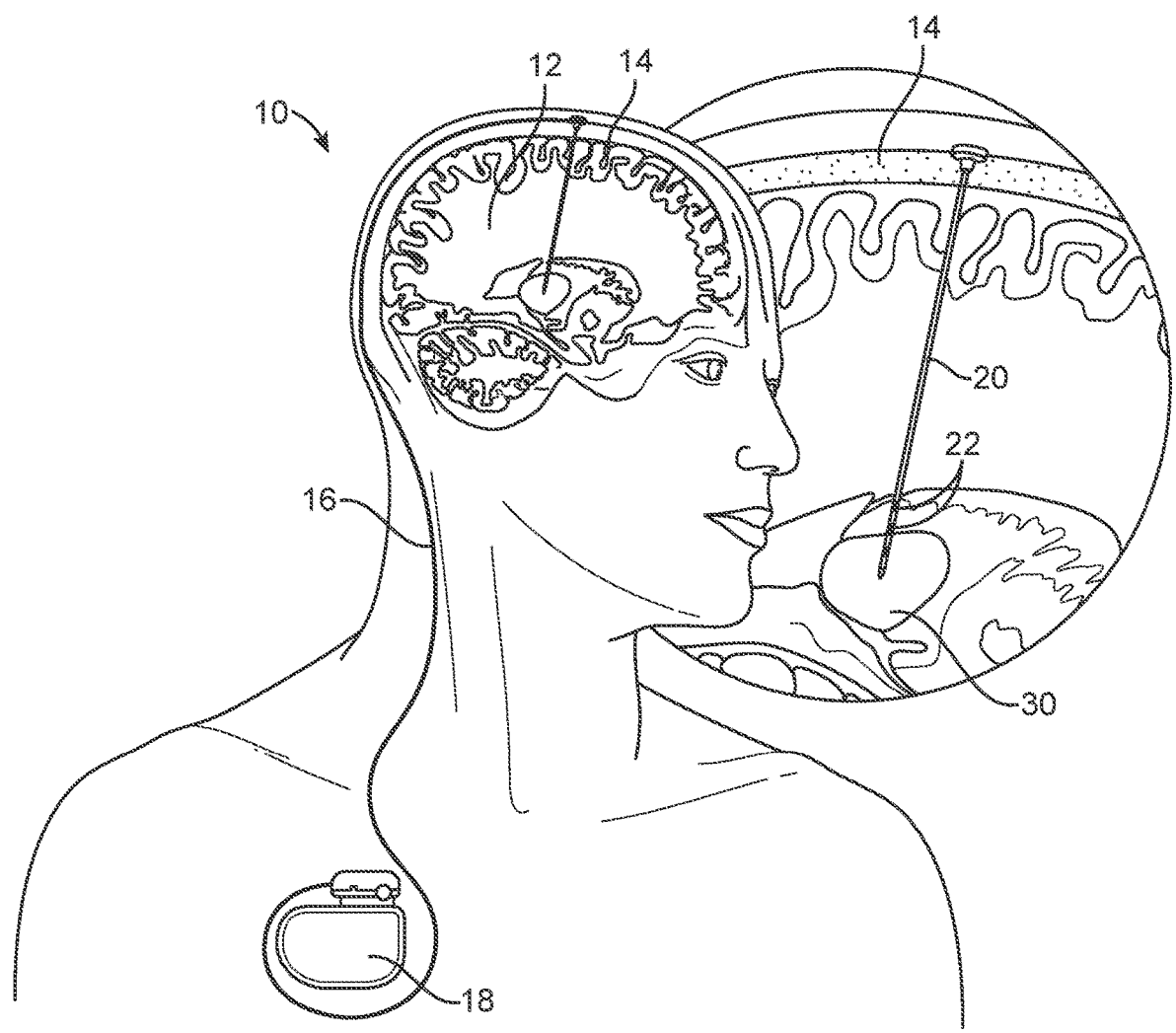
FIG. 1 illustrates a conventional deep brain stimulation device containing electrodes that are implanted within a brain of an individual.

Before the present invention is described, it is to be understood that this invention is not intended to be limited to particular embodiments or examples described, as such may, of course, vary. Further, when referring to the drawings like numerals indicate like elements.

Figure 2A:
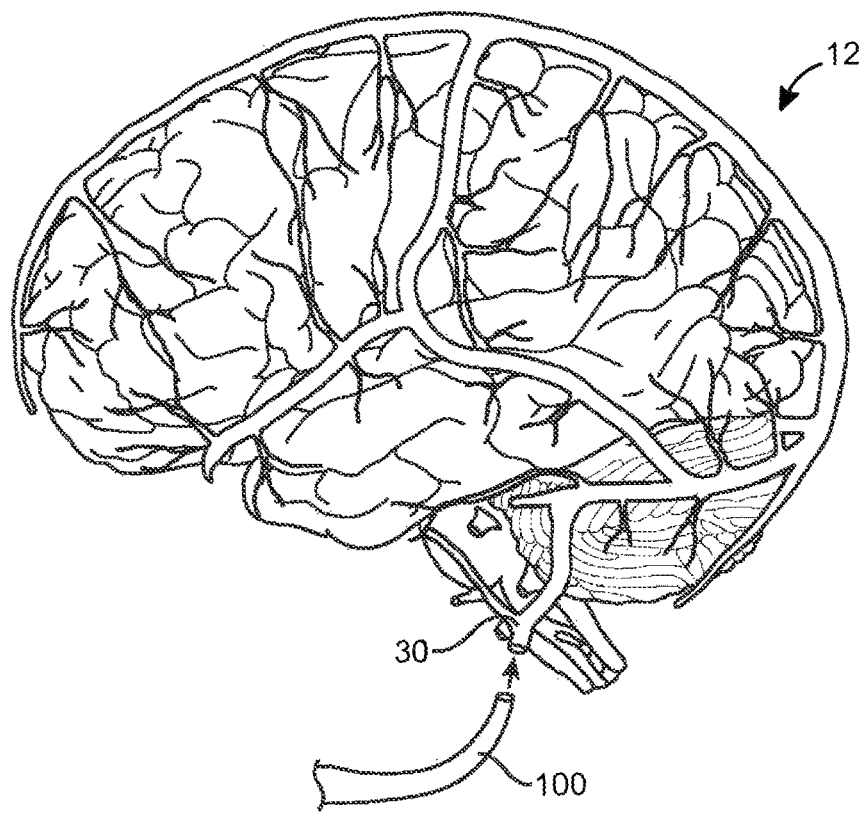
FIG. 2A illustrates a view of a vascular network of a brain 12 where a device 100 advances through a jugular vein 30 for advancement into deeper regions of brain tissue.

FIG. 2A illustrates a view of a vascular network of a brain 12 where a device 100 advances through a jugular vein 30 for advancement into deeper regions of brain tissue. The device 100 can be an access device that contains a device having a series of electrodes as discussed below. Alternatively, the device 100 can comprise a series of electrodes.

Figure 2B:
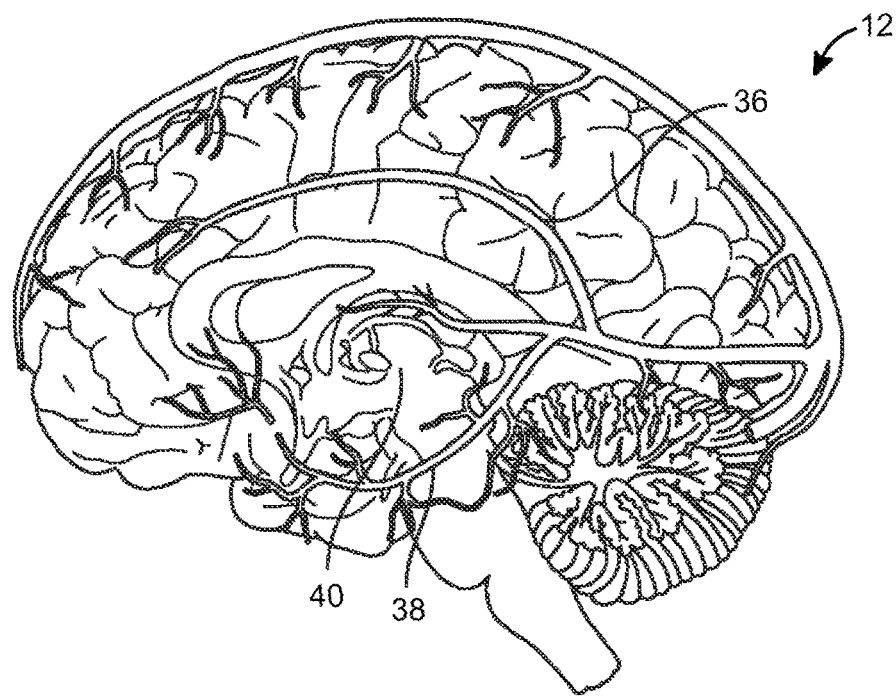
FIG. 2B illustrates a sectional view of the brain 12 of FIG. 2A taken along a mid-line of the brain 12 to illustrate a potential area of interest for treatment using DBS in accordance with the principles of this disclosure.

FIG. 2B illustrates a sectional view of the brain 12 of FIG. 2A taken along a mid-line of the brain 12 to illustrate a potential area of interest for treatment using deep brain stimulation ("DBS") in accordance with the principles of this disclosure. This illustration is intended to show a possible application of the methods and devices described herein. Clearly, the methods and devices can be used in any portion of the brain or anatomy (e.g., spine, renal nerves, etc.) where stimulation of an area is to be achieved through triangulation or application of energy to a combination of electrodes positioned about a region of interest.

FIG. 2B illustrates vessels used as an access path used to position one or more devices around an area of interest 40. For example, veins 36 (interior sagittal sinus) and 38 (basal vein of Rosenthal) can be used as a first and second region in the brain 12 for positioning of electrodes.

Figure 3A:
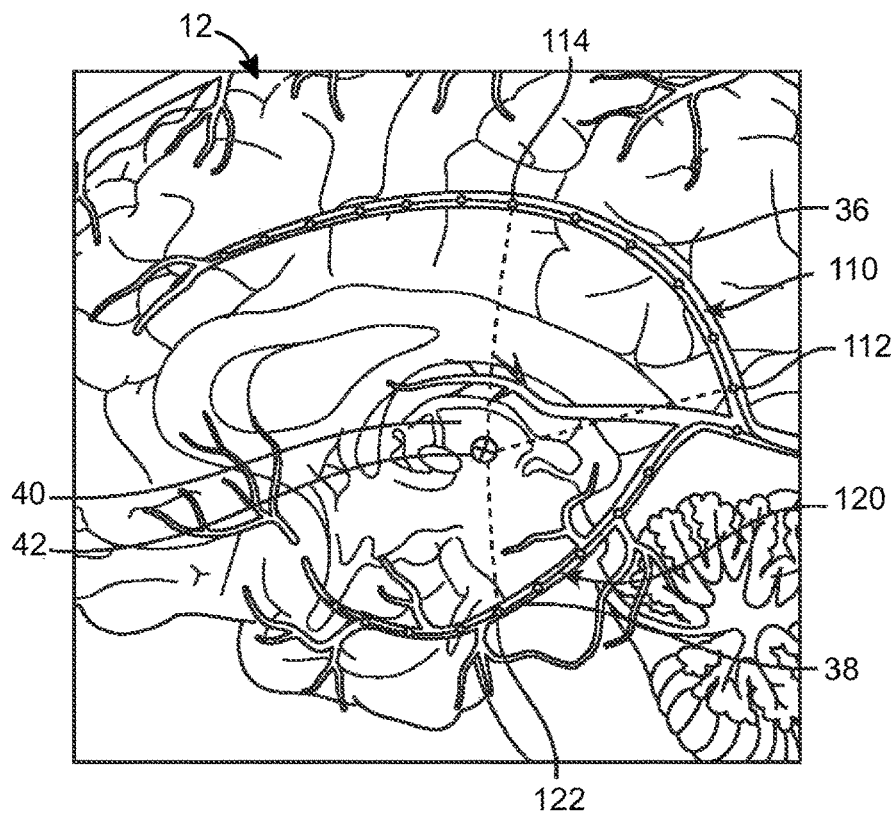
FIG. 3A illustrates a magnified area of the brain 12 showing a first series of electrodes 110 positioned in a first region of the brain 36 and a second series of electrodes 120 positioned in a second region of the brain 38.

FIG. 3A illustrates a magnified area of the brain 12 showing a first series of electrodes 110 positioned in a first vascular location in a first region 36 of the brain and a second series of electrodes 120 positioned in a first vascular location in a second region of the brain 38. As shown, the area of interest 40 is adjacent to and spaced from both the first region 36 of the brain and the second region 38 of the brain. The area of interest 40 is typically responsible or associated with the brain activity related to the condition attempted to be addressed by DBS. Furthermore, in this variation, the first region 36 of the brain is spaced from the second region 38 of the brain. In alternate variations, one or more electrodes can be positioned exterior to the vascular locations or directly in brain tissue.

As noted above, variations of the disclosure include using the vessels as paths to access brain tissue such that the series of electrodes can be inserted directly into brain tissue that is accessed from a vessel and avoids excessive trauma to brain tissue.

FIG. 3A also demonstrates the application of stimulation energy to any plurality of combination of electrodes selected from the first series of electrodes 110 and/or the second series of electrodes 120 to attempt to stimulate a region 42 in the area of interest 40. The plurality of combinations of electrodes illustrated in FIG. 3A shows three electrodes 112, 114, and 122 where electrodes 112 and 114 are positioned on the first series of electrodes 110 and electrode 122 is positioned on the second series of electrodes 120. However, any combination and any number of electrodes can be used to stimulate a region 42 in the area of interest 40, where each combination will stimulate a respective region of tissue 42 within the area. The various combination of electrodes will stimulate various different regions of tissue in the area of interest such that the physician can determine which combination of electrodes stimulates a region of tissue that produces a desirable outcome for the patient. In the illustrated variation, the electrodes are positioned about the basal ganglia and thalamus for purposes of illustration.

Figure 3B:
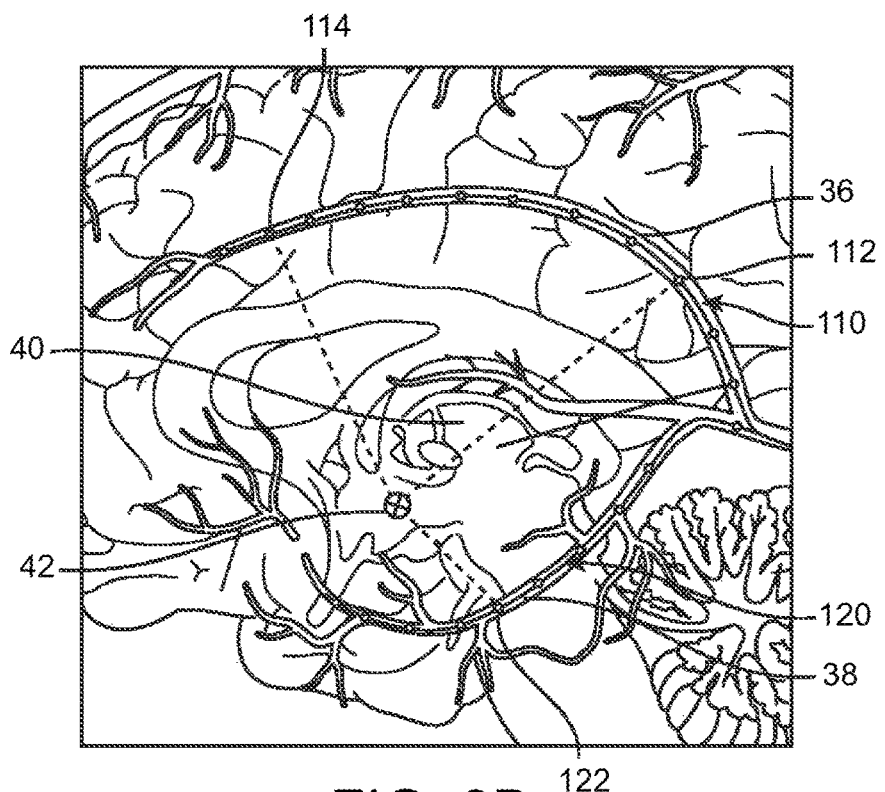
FIG. 3B illustrates the magnified area of the brain shown in FIG. 3A but with a different combination of electrodes that stimulates a different area in the region of interest.

FIG. 3B illustrates the magnified area of the brain shown in FIG. 3A but in this instance a different combination of electrodes 112, 114, and 122 is energized, which results in a stimulated region 42 that is in a different area than the region 42 of FIG. 3A. The altering of the combination of electrodes (any number of permutations using any number of electrodes) can result in an equivalent number of areas being stimulated. As noted herein, this triangulation can allow for locating the region that produces the optimal desired result for DBS therapy.

Furthermore, the combination of electrodes can be selected from a single series of electrode. In some variations, a single series of electrodes (rather than two series of electrodes) is positioned about a region of interest 40 sufficiently such that a combination of electrodes from a single series can apply stimulation energy to triangulate various regions in the area of interest. In one variation of the system and method, every permutation of combination of electrodes can be tried to determine the most effective target region that produces an associated brain activity required for the indication treated by the DBS. The application of energy to the different combinations of electrodes can produce different associated stimulated areas of tissue through adjustment of various electrical parameters applied by the controller (e.g., frequency, current, voltage, cycling of current between electrodes in the combination, etc.)

Identification of the region 42 can occur multiple ways. For example, various known brain activity scans can allow a physician to determine the outcome of the application of stimulation energy by any combination of electrodes. The scans can actually determine physical location of the desirable region 42. Alternatively, or in combination, identification of the physical location of the region 42 is not required. Instead, identification of the region occurs through measurement or patient outcomes. For example, if the DBS is intended to mediate the effects of tremors or Parkinson's disease, identification of the desirable combination of electrodes occurs when the patient's movement is controlled. Therefore, once the combination of electrodes is known application of stimulation energy produces a respective associated stimulated area that produces a benefit to the patient. In such a case, it may not be required to locate/identify the actual physical location of the associated stimulated area.

In some variations, treatment of the patient requires different combinations of electrodes over time. In such cases, if the DBS therapy declines in effectiveness over time, the system can perform additional algorithms to determine various additional permutations of combinations that might extend the effectiveness of the therapy. In some cases, stimulation may be constant, 24 hours a day. Alternatively, the pulse generator/controller can cycle on and off as needed or at a pre-determined time interval depending on the patient's condition.

Figure 4:
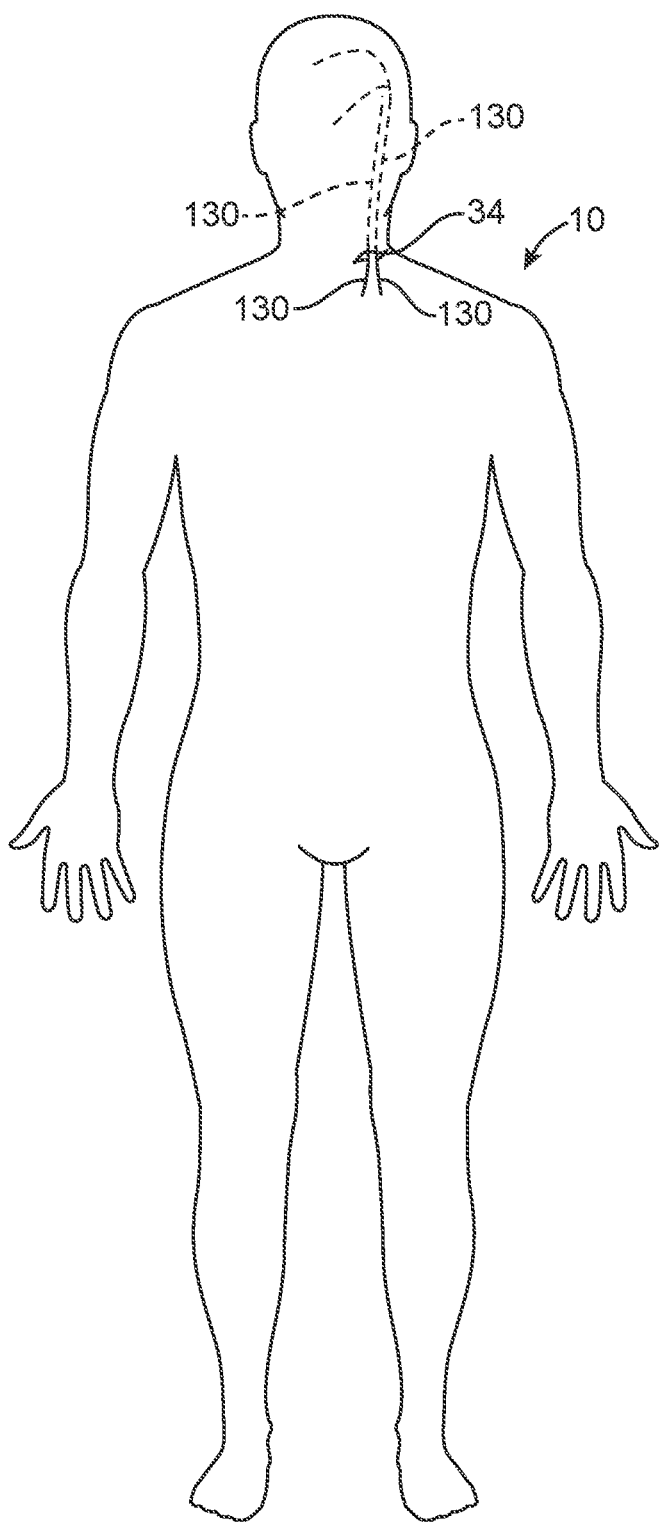
FIG. 4 illustrates a partial view of a patient 10 where one or more wires or members 130 that carry the electrodes exit the patient 10 via a jugular puncture site 34.

FIG. 4 illustrates a partial view of a patient 10 where one or more wires or members 130 that carry the electrodes exit the patient 10 via a jugular puncture site 34. Variations include the wires or members 130 contained in a sheath or covering. The wires 130 can include connectors or structures that allow for connection of the wires 130 to a telemetry unit or controller 18 (not shown in FIG. 4). In an alternate variation, the wires 130 can be implanted as discussed above in conventional DBS procedures.

Figure 5:
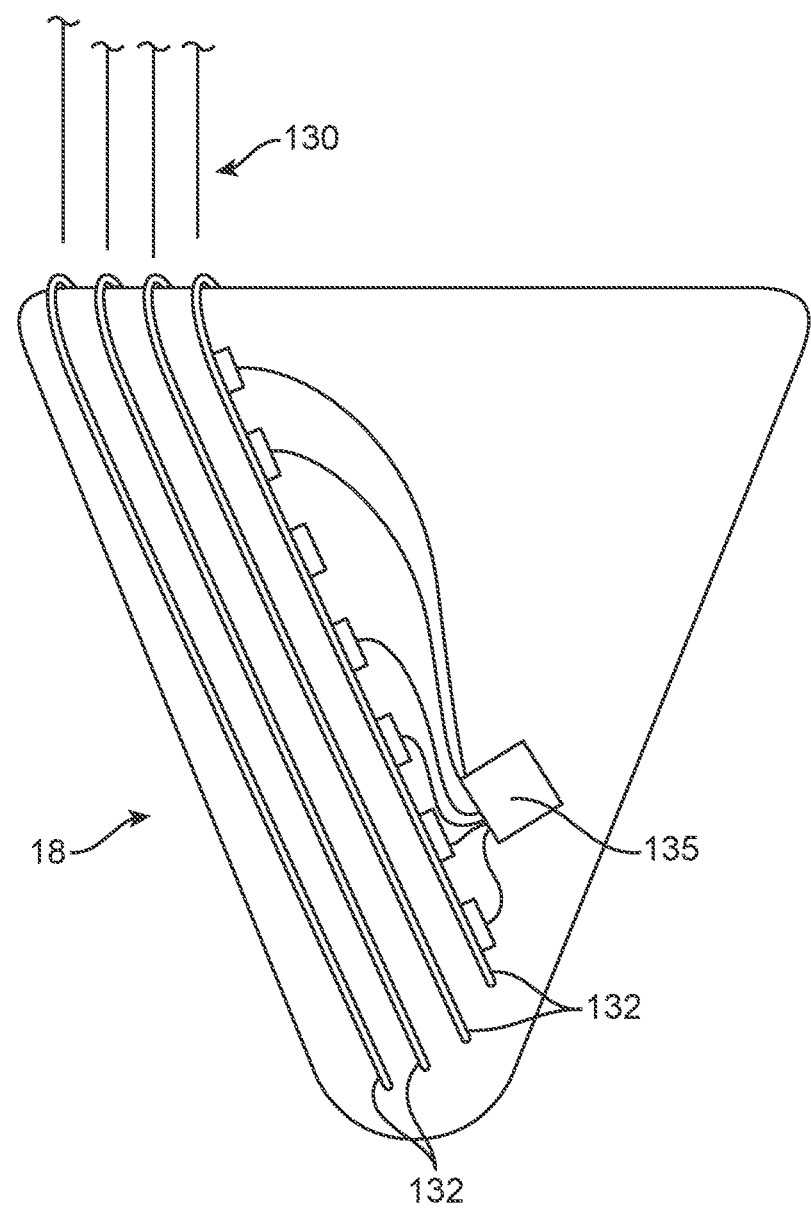
FIG. 5 illustrates a variation of a pulse generator or controller 18 for use with the systems described herein.

FIG. 5 illustrates a variation of a pulse generator or controller 18 for use with the systems described herein. As shown the controller 18 includes connectors such that each wire 130 can be individually connected to the controller 18. Each individual connector is electrically coupled to a transmitter or power supply 135 that delivers the treatment or stimulation energy to a respective electrode at a distal end of the wire 130. Although the illustrated variation shows 4 connectors 132, the number of connectors can vary depending on the configuration of the DBS system used.

Figure 6:
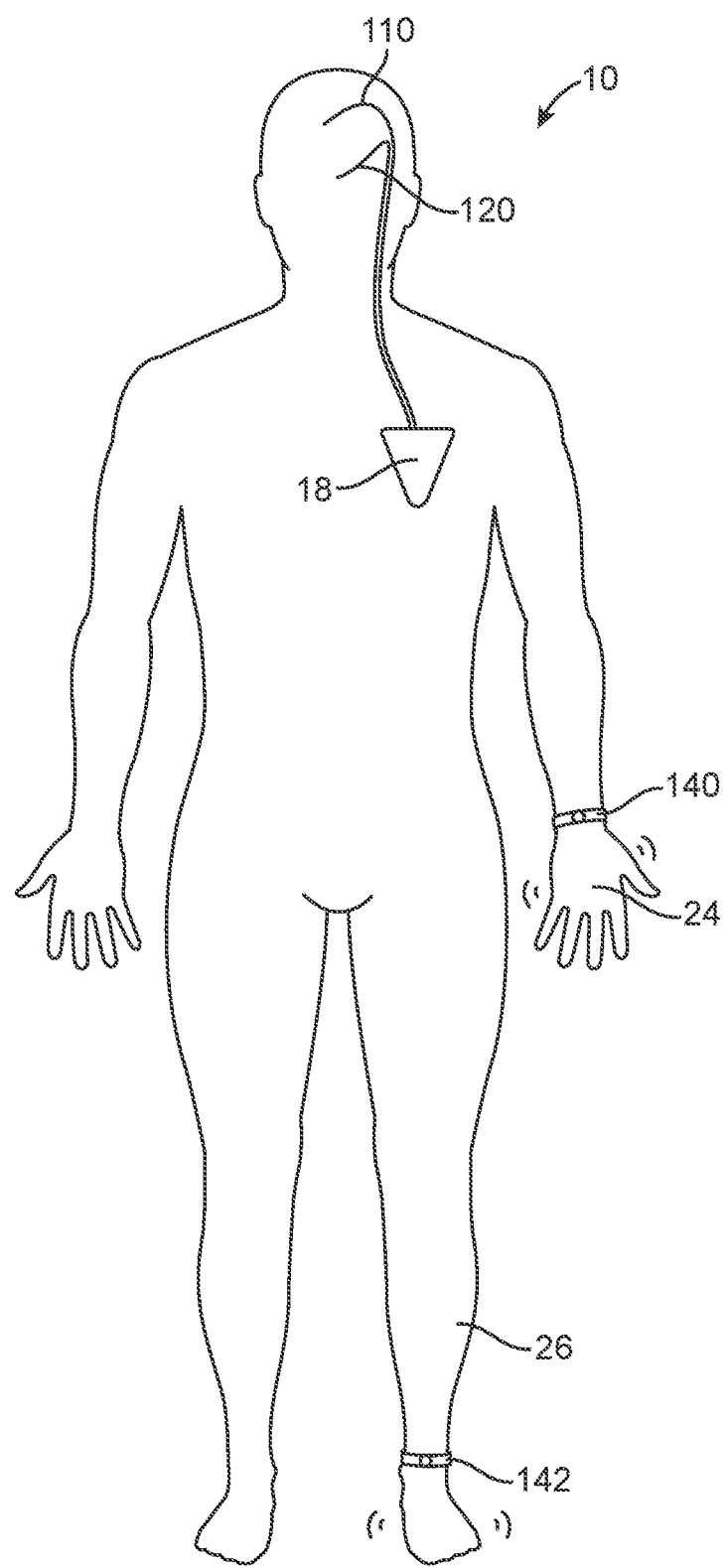
FIG. 6 illustrates one application of a system of the present disclosure for use in treating a patient 10 with Essential Tremor or Parkinson Disease.

FIG. 6 illustrates one application of a system of the present disclosure for use in treating a patient 10 with Essential Tremor or Parkinson Disease. As shown, a series of electrodes 110, 120 is implanted in the patient's cerebral tissue and are coupled to a controller/pacemaker 18. The system can stimulate through the combination of electrodes as discussed above to determine the effect on the patient 10. In certain variations, as shown, the patient 10 can be equipped with one or more devices 140, 142 that monitors movement. For example, such devices can comprise accelerometers that are affixed to the patient's hand 24 or leg 26. The devices 140 and/or 142 can communicate information to the controller 18 or an external monitoring system to determine the effects of the various combination of electrodes as they apply energy to the brain. The system can screen for increased and/or decreased movement of the patient 10. In certain variations, if the device 140 and/or 142 detects cessation or reduction of the involuntary movement by the patient 10, the controller 18 or external system can associate the particular electrode combination with the optimal effect.

Once the optimal combination of electrodes is determined, a variation of the system can further apply therapeutic energy to the combination of electrodes. In another variation, a neural network algorithm receives input from the one or more monitoring devices 140, 142 and controls stimulation via the controller 18. The algorithm can attempt all permutations of electrode combinations to triangulate the area that stimulation provides the best outcome. This determination can be performed while the patient is awake or conscious but sedated. The algorithm eventually determines the most effective combination to produce the desired result (e.g., reduction or cessation of involuntary movement) and repeats the stimulation to test the effectiveness of the selected combination.

Alternatively, the system can simply continue to provide stimulation energy to achieve the desired effect. In another variation, a location of the associated stimulation area is determined (as discussed above) so that a traditional DBS device 20 (e.g., shown in FIG. 1) can be implanted in that area.

Figure 7A:
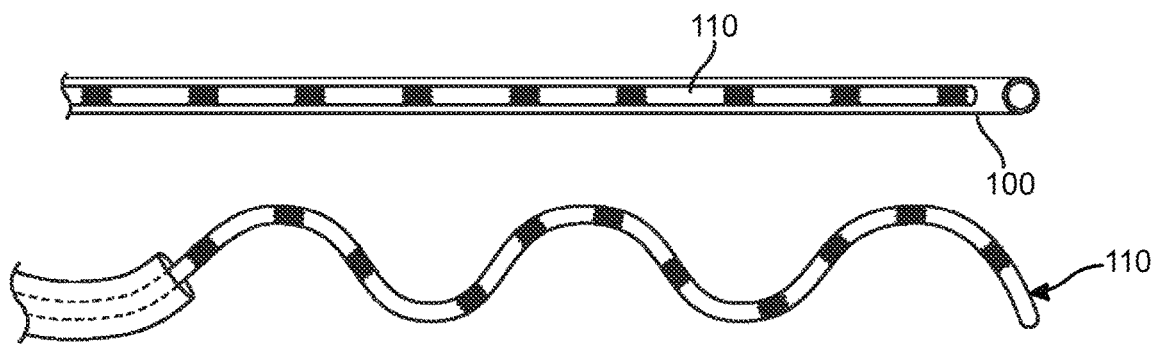
FIG. 7A illustrates an example of an electrode series that assists in maintaining positional stability of the implanted series of electrodes.

FIG. 7A illustrates an example of an electrode series that assists in maintaining positional stability of the implanted series of electrodes. As shown, the series of electrodes 110 can be positioned inside a micro-catheter or other access device 100 that is used to navigate the electrodes 110 within the vasculature. The series of electrodes 110 remains straight or follows the profile of the micro-catheter 100 while positioned therein. Once in a desired location, relative movement between the series of electrodes 110 and the access device 100 deploys the series of electrodes 110. Once deployed, the series of electrodes 110 can assume a non-linear shape (such as the serpentine shape illustrated) to provide sufficient radial force against the vessel. The non-linear shape can be helical, a simple bend, or any shape that allows for anchoring in the delicate vessels of the brain. Alternatively, the series of electrodes can be positioned on any structure that provides anchoring but does not restrict blood flow within the vessel.

Figure 7B:
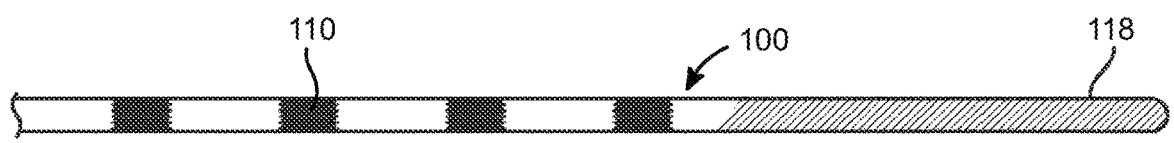
FIG. 7B illustrates a microwire with a distal end that is shapeable to provide torqueing and/or improve navigation through the veins

FIG. 7B illustrates a microwire with a series of electrodes 110 where a distal end 118 of the microwire is shapeable to provide torquing and/or improve navigation through the veins.

What is claimed is:

1. A method of stimulating a target region of a cerebral tissue of a brain, where the target region of cerebral tissue is associated with a brain activity of an individual, the method comprising:
    positioning a first elongate structure carrying a first series of electrodes in a first blood vessel which is a first region of the brain;
    positioning a second elongate structure carrying a second series of electrodes in a second blood vessel which is a second region of the brain;
    where the first region of the brain and the second region of the brain are spaced at a distance from the target region that is associated with the brain activity, where the target region is exterior to both the first blood vessel and the second blood vessel, and where the target region, the first region, and the second region are each spaced apart;
    anchoring the first elongate structure in the first region of the brain and anchoring the second elongate structure in the second region of the brain;
    repeatedly applying stimulation energy to a plurality of electrode combinations using a controller positioned on the individual, wherein each electrode combination comprises one or more electrodes from the first series of electrodes and/or one or more electrodes from the second series of electrodes, where application of stimulation energy to each electrode combination produces at least a first stimulated area of cerebral tissue associated with a first electrode combination and a second stimulated area of cerebral tissue associated with a second electrode combination, where the first stimulated area is in a different area of cerebral tissue than and spaced from the second stimulated area such that stimulation of the first stimulated area produces a first effect in the individual and stimulation of the second stimulated area produces a second effect in the individual;
    identifying a target combination of electrodes such that the first stimulated area or the second stimulated area stimulates the target region associated with the brain activity; and
    using a device affixed to the individual to communicate information to the controller to determine the effects of the stimulation energy.

2. The method of claim 1, where the plurality of electrode combinations comprises at least three electrodes selected from the first series of electrodes and/or the second series of electrodes.

3. The method of claim 1, where the brain activity controls a muscle movement.

4. The method of claim 1, further comprising monitoring a portion of the individual for movement and associating increased or decreased movement of the portion of the individual when applying stimulation to the target region using the target combination of electrodes.

5. The method of claim 4, where monitoring the portion of the individual for movement comprises using an accelerometer device on a hand or leg of the individual.

6. The method of claim 1, where repeatedly applying stimulation energy to the plurality of electrode combinations selected from the first series of electrodes and/or the second series of electrodes comprises determining every permutation of at least three electrodes and applying stimulation energy to every permutation until identifying the target combination of electrodes and the target region.

7. The method of claim 6, further comprising pausing between applying stimulation energy to each combination of electrodes.

8. The method of claim 1, further comprising applying a therapeutic energy to the target combination of electrodes to treat the target region.

9. The method of claim 1, further comprising applying a therapeutic energy to the target region using at least one second therapy electrode device.

10. The method of claim 1, where the first blood vessel is accessed by advancing the first series of electrodes through a vessel outside of the brain.

11. The method of claim 10, where the second blood vessel is accessed by advancing the second series of electrodes through the vessel outside of the brain.

12. The method of claim 1, further comprising obtaining a non-invasive image of the brain to correlate the target region with at least one anatomical feature.

13. A method of stimulating a cerebral tissue of a brain, where the cerebral tissue is associated with a brain activity of an individual, the method comprising:
    positioning a first elongate structure carrying a first series of electrodes in a first blood vessel which is a first region of the brain;
    positioning a second elongate structure carrying a second series of electrodes in a second blood vessel which is a second region of the brain;
    where the first region of the brain and the second region of the brain are located at a distance from the cerebral tissue that is associated with the brain activity, and where, the first region, and the second region are each spaced apart;
    anchoring the first elongate structure in the first region of the brain and anchoring the second elongate structure in the second region of the brain;
    repeatedly applying stimulation energy to a plurality of electrode combinations using a controller positioned on the individual, wherein each electrode combination comprises one or more electrodes from the first series of electrodes and/or one or more electrodes from the second series of electrodes, where application of stimulation energy to each electrode combination produces at least a first stimulated area of cerebral tissue associated with a first electrode combination and a second stimulated area of cerebral tissue spaced from the first stimulated area and associated with a second electrode combination, where the first stimulated area is in a different region of cerebral tissue than the second stimulated area;

identifying whether the first stimulated area or the second stimulated area comprises a target region of cerebral tissue that affects the brain activity;

applying therapeutic energy to the target region; and using a device affixed to the individual to communicate information to the controller to determine the effects of the stimulation energy.

* * * * *